(12) United States Patent
Fourkas et al.

(10) Patent No.: US 9,241,753 B2
(45) Date of Patent: Jan. 26, 2016

(54) SKIN PROTECTION FOR SUBDERMAL CRYOGENIC REMODELING FOR COSMETIC AND OTHER TREATMENTS

(71) Applicant: MyoScience, Inc., Redwood City, CA (US)

(72) Inventors: Michael Fourkas, Sunnyvale, CA (US); Ronald Williams, Menlo Park, CA (US); John Allison, Redwood City, CA (US)

(73) Assignee: MyoScience, Inc., Fremont, CA (US)

( * ) Notice: Subject to any disclaimer, the term of this patent is extended or adjusted under 35 U.S.C. 154(b) by 196 days.

(21) Appl. No.: 13/741,350

(22) Filed: Jan. 14, 2013

(65) Prior Publication Data

US 2013/0184695 A1  Jul. 18, 2013

Related U.S. Application Data

(60) Provisional application No. 61/586,692, filed on Jan. 13, 2012.

(51) Int. Cl.
*A61B 18/02* (2006.01)
*A61L 31/08* (2006.01)
*A61L 31/14* (2006.01)
(Continued)

(52) U.S. Cl.
CPC ............... *A61B 18/02* (2013.01); *A61L 31/088* (2013.01); *A61L 31/14* (2013.01); *A61B 2017/00473* (2013.01); *A61B 2017/00747* (2013.01); *A61B 2017/00761* (2013.01); *A61B 2018/00041* (2013.01); *A61B 2018/00089* (2013.01); *A61B 2018/00095* (2013.01); *A61B 2018/00148* (2013.01); *A61B 2018/00458* (2013.01); *A61B 2018/0293* (2013.01); *A61L 2400/18* (2013.01); *A61L 2430/40* (2013.01)

(58) Field of Classification Search
CPC ............... A61B 18/02; A61B 18/0218; A61B 2018/02; A61B 2018/0262; A61B 2018/0293
See application file for complete search history.

(56) References Cited

U.S. PATENT DOCUMENTS 2,319,542 A  5/1943  Hall
2,672,032 A  3/1964  Towse
(Continued)

FOREIGN PATENT DOCUMENTS

CA  2643474 A1  9/2007
EP  0043447 A2  6/1981
(Continued)

OTHER PUBLICATIONS

Har-Shai et al., "Effect of skin surface temperature on skin pigmentation during contact and intralesional cryosurgery of hypertrophic scars and Kleoids," Journal of the European Academy of Dermatology and Venereology, Feb. 2007, vol. 21, issue 2, pp. 191-198.
(Continued)

*Primary Examiner* — Joseph Stoklosa
*Assistant Examiner* — Eunhwa Kim
(74) *Attorney, Agent, or Firm* — Kilpatrick Townsend and Stockton LLP

(57) ABSTRACT

A cryogenic needle probe having a proximal and distal region. A cooling supply tube provides pressurized cooling fluid within the needle. The proximal region is more conductive that the distal region. The proximal region is conductively coupled to a heat source.

16 Claims, 8 Drawing Sheets

(51) Int. Cl.
  *A61B 18/00*  (2006.01)
  *A61B 17/00*  (2006.01)

(56) References Cited

U.S. PATENT DOCUMENTS

| | | |
|---|---|---|
| 3,266,492 A | 8/1966 | Steinberg |
| 3,289,424 A | 12/1966 | Lee |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A | 8/1990 | Merry et al. |
| 5,059,197 A | 10/1991 | Urie et al. |
| 5,200,170 A | 4/1993 | McDow |
| 5,294,325 A | 3/1994 | Liu |
| 5,334,181 A | 8/1994 | Rubinsky et al. |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,814,040 A | 9/1998 | Nelson et al. |
| 5,860,970 A | 1/1999 | Goddard et al. |
| 5,879,378 A | 3/1999 | Usui |
| 5,899,897 A | 5/1999 | Rabin et al. |
| 5,916,212 A | 6/1999 | Baust et al. |
| 5,957,963 A * | 9/1999 | Dobak, III ................ 607/104 |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 | 2/2001 | Dobak, III |
| 6,196,839 B1 | 3/2001 | Ross |
| 6,238,386 B1 | 5/2001 | Muller et al. |
| 6,277,099 B1 | 8/2001 | Strowe et al. |
| 6,277,116 B1 | 8/2001 | Utely et al. |
| 6,363,730 B1 | 4/2002 | Thomas et al. |
| 6,371,943 B1 | 4/2002 | Racz et al. |
| 6,432,102 B2 | 8/2002 | Joye et al. |
| 6,494,844 B1 | 12/2002 | Van Bladel et al. |
| 6,503,246 B1 | 1/2003 | Har-Shai et al. |
| 6,506,796 B1 | 1/2003 | Fesus et al. |
| 6,546,935 B2 | 4/2003 | Hooven |
| 6,551,309 B1 | 4/2003 | LePivert |
| 6,562,030 B1 | 5/2003 | Abboud et al. |
| 6,629,951 B2 | 10/2003 | Laufer et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,902,554 B2 | 6/2005 | Huttner |
| 6,905,492 B2 | 6/2005 | Zvuloni et al. |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,195,616 B2 | 3/2007 | Diller et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 | 8/2009 | Bleich et al. |
| 7,641,679 B2 | 1/2010 | Joye et al. |
| 7,713,266 B2 | 5/2010 | Elkins et al. |
| 7,803,154 B2 | 9/2010 | Toubia et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,715,275 B2 | 5/2014 | Burger et al. |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0181896 A1 | 9/2003 | Zvuloni et al. |
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |

(56) References Cited

U.S. PATENT DOCUMENTS

| | | |
|---|---|---|
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1* | 6/2007 | Elkins et al. .................. 606/21 |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299357 A1 | 12/2009 | Zhou |
| 2010/0198207 A1 | 8/2010 | Elkins et al. |
| 2011/0144631 A1 | 6/2011 | Elkins et al. |
| 2012/0065629 A1 | 3/2012 | Elkins et al. |
| 2012/0089211 A1 | 4/2012 | Curtis et al. |
| 2012/0265187 A1 | 10/2012 | Palmer, III et al. |
| 2013/0324990 A1 | 12/2013 | Burger et al. |
| 2014/0249519 A1 | 9/2014 | Burger et al. |

FOREIGN PATENT DOCUMENTS

| | | |
|---|---|---|
| EP | 0777123 A1 | 6/1997 |
| EP | 0955012 A1 | 11/1999 |
| EP | 1074273 A1 | 2/2001 |
| EP | 1377327 B1 | 9/2007 |
| EP | 1862125 A2 | 12/2007 |
| GB | 1360353 B | 7/1974 |
| GB | 1402632 A | 8/1975 |
| JP | 60-013111 | 1/1985 |
| JP | H04-357945 A | 12/1992 |
| JP | 05-038347 | 2/1993 |
| JP | 10-014656 A | 1/1998 |
| JP | 2001-178737 A | 7/2001 |
| JP | 2004-511274 A | 4/2004 |
| JP | 2005-080988 A | 3/2005 |
| JP | 2006-130055 A | 5/2006 |
| JP | 2006-517118 A | 7/2006 |
| JP | 2008-515469 A | 5/2008 |
| RU | 2254060 | 6/2005 |
| WO | 97/49344 A1 | 12/1997 |
| WO | 01/97702 A1 | 12/2001 |
| WO | 02/02026 A1 | 1/2002 |
| WO | 02/092153 A2 | 11/2002 |
| WO | 2004/039440 A1 | 5/2004 |
| WO | 2004/045434 A | 6/2004 |
| WO | 2004/089460 A2 | 10/2004 |
| WO | 2005/000106 A2 | 1/2005 |
| WO | 2005/079321 A2 | 9/2005 |
| WO | 2005/096979 A1 | 10/2005 |
| WO | 2006/012128 A2 | 2/2006 |
| WO | 2006/023348 A1 | 3/2006 |
| WO | 2006/044727 A2 | 4/2006 |
| WO | 2006/062788 A2 | 6/2006 |
| WO | 2006/125835 A1 | 11/2006 |
| WO | 2006/127467 A2 | 11/2006 |
| WO | 2007/025106 A2 | 3/2007 |
| WO | 2007/037326 A1 | 4/2007 |
| WO | 2007/089603 A2 | 8/2007 |
| WO | 2007/129121 A1 | 11/2007 |
| WO | 2007/135629 A1 | 11/2007 |
| WO | 2009/026471 A1 | 2/2009 |
| WO | 2009/146053 A1 | 12/2009 |
| WO | 2010/075438 A1 | 7/2010 |
| WO | 2010/075448 A1 | 7/2010 |

OTHER PUBLICATIONS

Advanced Cosmetic Intervention, Inc. [webpage], retrieved from the Internet: <<http://www.acisurgery.com>>, copyright 2007, 1 page.

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

Cryosurgical Concepts, Inc., [webpage] "CryoProbe™", retrieved from the Internet: <<http://www.cryo-surgical.com//>> on Feb. 8, 2008, 2 pages total.

Dasiou-Plankida, "Fat injections for facial rejuvenation: 17 years experience in 1720 patients," Journal of Cosmetic Dermatology, Oct 22, 2004; 2(3-4): 119-125.

Foster et al., "Radiofrequency Ablation of Facial Nerve Branches Controlling Glabellar Frowning", Dermatol Surg. Dec. 2009; 35(12):1908-1917.

Har-Shai et al., "Effect of skin surface temperature on skin pigmentation during contact and intralesional cryosurgery of hypertrophic scars and Kleoids," Journal of the European Academy of Dermatology and Venereology 21 (2):191-198.

Magalov et al., "Isothermal volume contours generated in a freezing gel by embedded cryo-needles with applications to cryo-surgery," Cryobiology Oct. 2007, 55(2):127-137.

Metrum CryoFlex, Cryoablation in pain management brochure, 2012, 5 pages.

Metrum CryoFlex, Cryosurgery probes and accessories catalogue, 2009, 25 pages.

One Med Group, LLC., [webpage] "CryoProbe™", retrieved from the Internet: << http://www.onemedgroup.com/>> on Feb. 4, 2008, 2 pages total.

Rewcastle et al., "A model for the time dependent three-dimensional thermal distribution within iceballs surrounding multiple cryoprobes," Med Phys. Jun. 2001;28(6):1125-1137.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

(56) References Cited

OTHER PUBLICATIONS

Utley et al., "Radiofrequency Ablation of the Nerve to the Corrugator Muscle for the Elimination of Glabellar Furrowing," Arch. Facial Plastic Surgery 1: 46-48, 1999.

Yang et al., "Apoptosis induced by cryo-injury in human colorectal cancer cells is associated with mitochondrial dysfunction.," International Journal of Cancer, 2002, vol. 103, No. 3, pp. 360-369.

U.S. Appl. No. 61/116,050, filed Nov. 19, 2008, titled "Cryosurgical Safety Valve Arrangement and Methods for Its Use in Cosmetic and Other Treatment" by Timothy Holland et al.

International Search Report and Written Opinion mailed Apr. 19, 2013, from PCT Application No. PCT/US2013/021488, 12 pages.

International Preliminary Report on Patentability mailed Jul. 24, 2014, from PCT Application No. PCT/US2013/021488, 6 pages.

\* cited by examiner

SKIN PROTECTION FOR SUBDERMAL CRYOGENIC REMODELING FOR COSMETIC AND OTHER TREATMENTS

This application claims the benefit of U.S. Provisional Application No. 61/586,692, filed on Jan. 13, 2012, the entirety of which is incorporated by reference herein.

BACKGROUND

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. Other embodiments may find use for a wide range of medical indications. The remodeling of the target tissue may achieve a desired change in its behavior or composition.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary enervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, improved medical devices, systems, and methods utilizing a cryogenic approach to treating the tissue have been proposed, particularly for treatment of wrinkles, fat, cellulite, and other cosmetic defects. These new techniques can provide an alternative visual appearance improvement mechanism which may replace and/or compliment known bioactive and other cosmetic therapies, ideally allowing patients to decrease or eliminate the injection of toxins and harmful cocktails while providing similar or improved cosmetic results. These new techniques are also promising because they may be performed percutaneously using only local or no anesthetic with minimal or no cutting of the skin, no need for suturing or other closure methods, no extensive bandaging, and limited or no bruising or other factors contributing to extended recovery or patient "down time." Additionally, cryogenic treatments are also desirable since they may be used in the treatment of other cosmetic and/or dermatological conditions (and potentially other target tissues), particularly where the treatments may be provided with greater accuracy and control, less collateral tissue injury and/or pain, and greater ease of use.

While these new cryogenic treatments are promising, careful control of temperature along the cryogenic probe is necessary in order to obtain desired results in the target treatment area as well as to avoid unwanted tissue injury in adjacent areas. Once the probe is introduced into a target treatment area, cooling fluid flows through the probe and probe temperature decreases proximally along the length of the probe toward the probe hub. A proximal portion of the probe and hub is in contact with and pierces the skin. The hub may be positioned at a fixed location along the probe or may move independent to the probe allowing the probe to be inserted to variable depths while retaining skin contact. This region of the probe can become very cold which can damage the skin in the form of blistering or loss of pigmentation. Therefore, it would be desirable to provide a cryogenic device that helps control temperature directly at a proximal shaft portion of the probe thereby minimizing unwanted tissue cooling and damage.

BRIEF SUMMARY OF THE INVENTION

Embodiments of the invention provide improved medical devices, systems, and methods. Many of the devices and systems described herein will be beneficial for cryogenically remodeling target tissue while protecting non-target tissue.

One embodiment of the invention relates to a method for cryogenically treating tissue. In the method, a needle probe shaft can be provided having a distal portion and a proximal portion. The needle probe shaft can have a first conductivity at the distal portion and a second conductivity at the proximal portion. The second conductivity is greater than the first conductivity. The least one tissue needle probe shaft can be penetrated into non-target tissue layered under target tissue, such that a distal portion of the needle probe shaft is positioned in the target tissue and the proximal portion of the needle probe shaft is positioned in the non-target tissue. The target tissue can be cooled via the distal portion of the needle probe shaft to affect remodeling of the target tissue. Energy can be directly conducted via the proximal portion of the needle probe shaft while cooling the target tissue, thereby limiting cooling of the non-target tissue.

In one aspect, the non-target tissues includes skin.

In a further aspect, limiting cooling prevents discoloration of the skin.

In a further aspect, the non-target tissues may include at least a portion of subcutaneous tissue.

In a further aspect, cooling zones formed in the target tissue can terminate proximally about a distal end of the second conductive material.

In a further aspect, remodeling the tissue causes nerve signal conduction disruption within the target tissue.

In a further aspect, the needle probe shaft comprises a first conductive material at the distal portion and a second conductive material at the proximal portion, wherein the second material is more conductive than the first material.

In a further aspect, the second conductive material can be conductively coupled to a heat source.

In a further aspect, the heat source can provide the second conductive material with 0.5-3.0 Watts during cooling.

In a further aspect, conducting energy can provide energy to affect a phase change of the liquid coolant to a gas at the proximal portion and/or joule thompson.

In a further aspect, the first conductive material can be stainless steel.

In a further aspect, the second conductive material includes at least one layer of metal over the stainless steel.

In a further aspect, the metal can be gold.

In a further aspect, the proximal portion of the needle shaft has greater mass than the distal portion of the needle shaft.

In a further aspect, the proximal portion of the needle shaft has a greater wall thickness than the distal portion of the needle shaft.

Another embodiment of the invention relates to an apparatus for cryogenically treating tissue. The apparatus can include a housing having a proximal and distal end, the housing including a heat source. At least one needle probe shaft can extend from the distal end of the housing and have a distal needle shaft portion and a proximal needle shaft portion. The proximal needle shaft portion is more conductive than the distal needle shaft portion. A cooling supply tube can be internally housed within elongate needle. The cooling supply tube can have an exit within the elongate needle.

In a further aspect, the at least one needle probe shaft can include a first conductive material externally exposed at the distal portion and a second conductive material conductively coupled to the first material at the proximal shaft portion. The second material can be more conductive than the first material.

In a further aspect, the first conductive material of the apparatus can be stainless steel.

In a further aspect, the second conductive material of the apparatus can be a cladding of metal over the stainless steel.

In a further aspect, the metal of the cladding can be gold.

In a further aspect, the heat source of the apparatus can be configured to provide the second conductive material with 0.5-3.0 Watts.

In a further aspect, an array of needle probes of the apparatus can extend from the housing.

In a further aspect, the array can include three linearly arranged needle probes.

In a further aspect, the at least one needle probe shaft of the apparatus is 0.3-0.6 cm in length and the second conductive material terminates approximately 2 mm from the distal shaft portion.

In a further aspect, the housing of the apparatus further includes a cooling source coupled to the cooling supply tube.

In a further aspect, wherein the proximal shaft portion has greater mass than the distal shaft portion.

In a further aspect, the proximal shaft portion has a greater wall thickness than the distal shaft portion.

In a further aspect, the at least one needle probe shaft is coated with a polymer.

DETAILED DESCRIPTION OF THE INVENTION

Figure 1A:
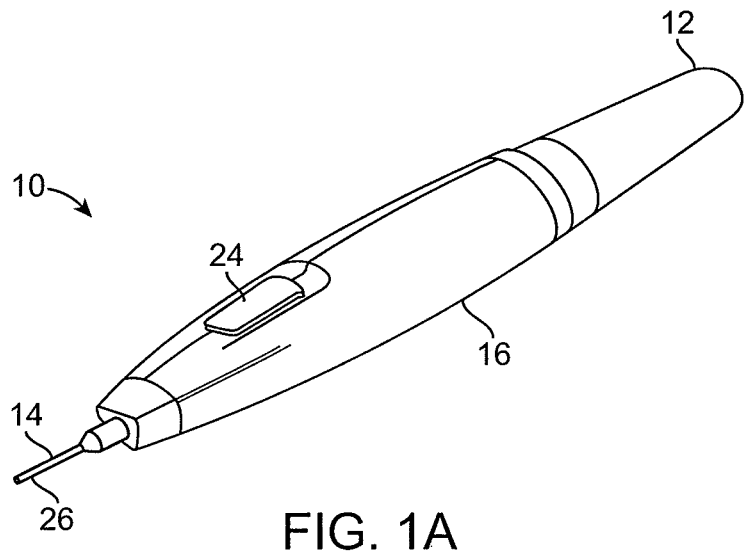
FIG. 1A is a perspective view of a self-contained subdermal cryogenic remodeling probe and system, according to an embodiment of the invention.

The present invention provides improved medical devices, systems, and methods. Embodiments of the invention will facilitate remodeling of target tissues disposed at and below the skin, optionally to treat a cosmetic defect, a lesion, a disease state, and/or so as to alter a shape of the overlying skin surface, while providing protection to portions of non-target tissues, including the skin, which are directly above the target tissues.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a permanent treatment that limits or avoids inflammation and mobilization of skeletal muscle satellite repair cells. In some embodiments, temporary axonotmesis or neurotmesis degeneration of a motor nerve is desired, which may be induced using treatment temperatures from about −25° C. to about −90° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", and U.S. patent application Ser. No. 13/325,004 entitled "Method for Reducing Hyperdynamic Facial Wrinkles", the full disclosures of which are each incorporated by reference herein.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms as disclosed in commonly assigned U.S. Pub. No. 2009/0248001 entitled "Pain Management Using Cryogenic Remodeling," the full disclosure of which is incorporated herein by reference.

Figure 1B:
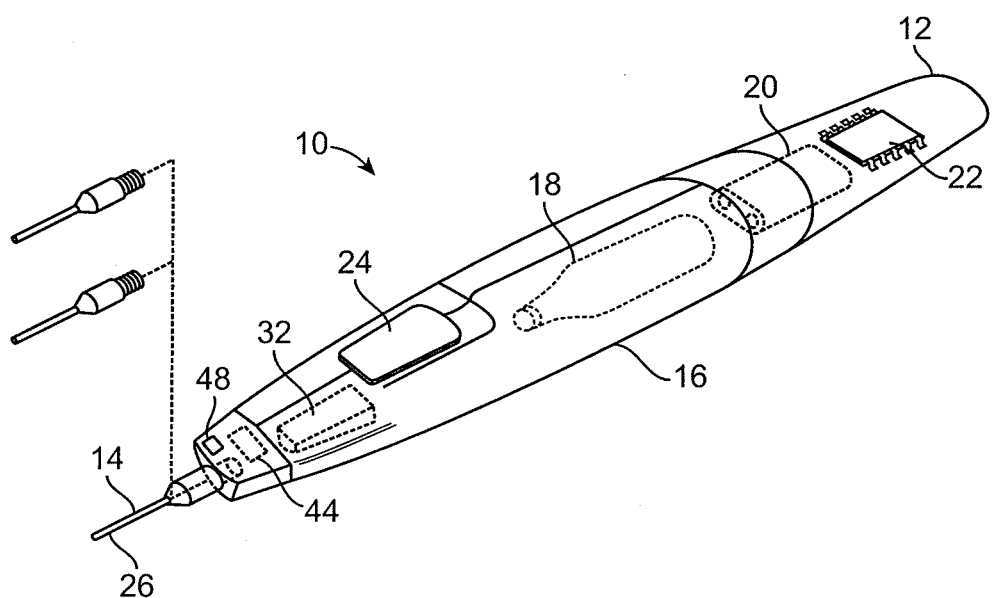
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 thereby helping to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about 0.5 mm and 5 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 is releasably coupled with body 16 so that it may be replaced after use with a sharper needle (as indicated by the dotted line) or with a needle having a different configuration. In exemplary embodiments, the needle may be threaded into the body, it may be press fit into an aperture in the body or it may have a quick disconnect such as a detent mechanism for engaging the needle with the body. A quick disconnect with a check valve is advantageous since it permits decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature is also advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 comprises a canister, sometimes referred to herein as a cartridge, containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery or wall source. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 comprises a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2:
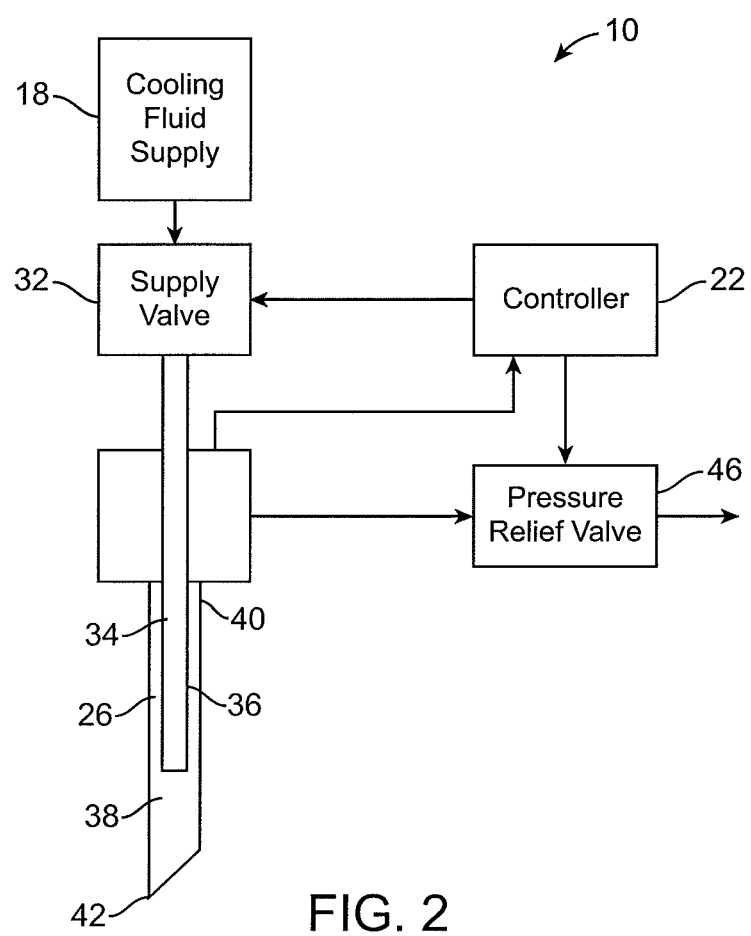
FIG. 2 schematically illustrates components that may be included in the treatment system.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2, an optional heater (not illustrated) may be used to heat cooling fluid supply 18 so that heated cooling fluid flows through valve 32 and through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 entitled "Dermal and Transdermal Cryogenic Microprobe Systems and Methods," the entire contents of which are incorporated herein by reference. Previously incorporated U.S. Patent Publication No. 2008/0200910 discloses additional details on the needle 26 along with various alternative embodiments and principles of operation. In some embodiments safety mechanism can be included so that the cooling supply is not overheated. Examples of such embodiments are disclosed in commonly assigned Int'l. Pub. No. WO 2010075438, the entirety of which is incorporated by reference herein.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve allows better temperature control in the needle, minimizing transient temperatures. Further details on exhaust volume are disclosed in previously incorporated U.S. Pat. Pub. No. 2008/0200910.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154,254.

Figure 3A:
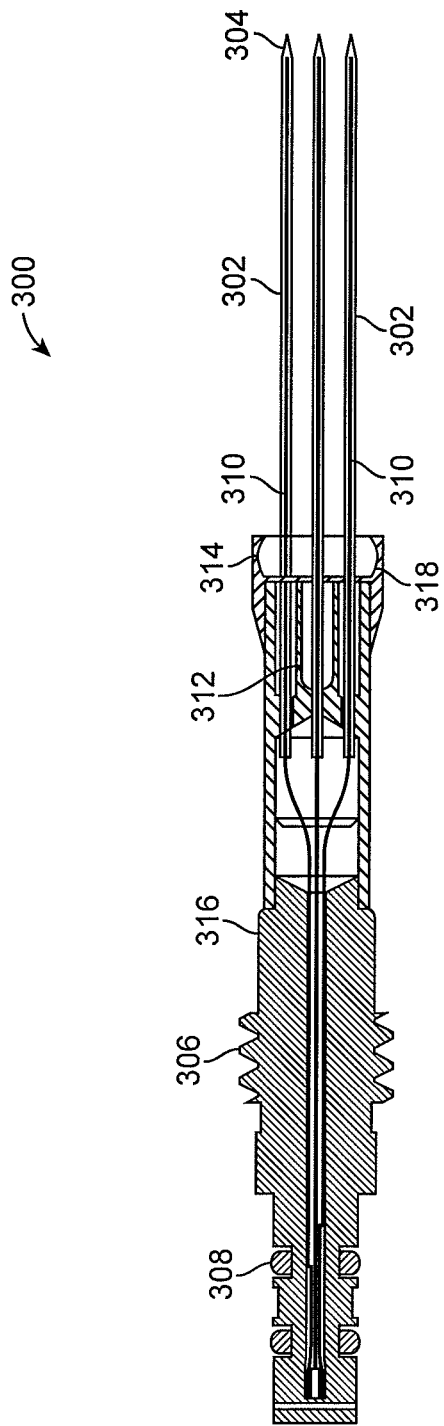
FIGS. 3A-3C illustrate needle probes, according to various embodiments of the invention.

Turning now to FIG. 3A, an exemplary embodiment of probe 300 having multiple needles 302 is described. In FIG. 3A, probe housing 316 includes threads 306 that allow the probe to be threadably engaged with the housing 16 of a cryogenic device. O-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. Using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment.

However, as the cooling fluid flows through the probe 316, probe temperature decreases proximally along the length of the needle shafts 302 towards the probe hub 318. The proximal portion of needle shaft 302 and the probe hub 318 contact skin and become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. In one embodiment, a solution to this challenge is to include a heater element 312 that can heat the proximal portion of needle shaft 302 and an optional temperature sensor 314 to monitor temperature in this region. To further this, the a proximal portion of the needle shaft 302 can be a highly conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1KΩ, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. In at least some instances, the cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cyrogenic Remodelling for Cosmetic and Other Treatments", the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

Figure 3B:
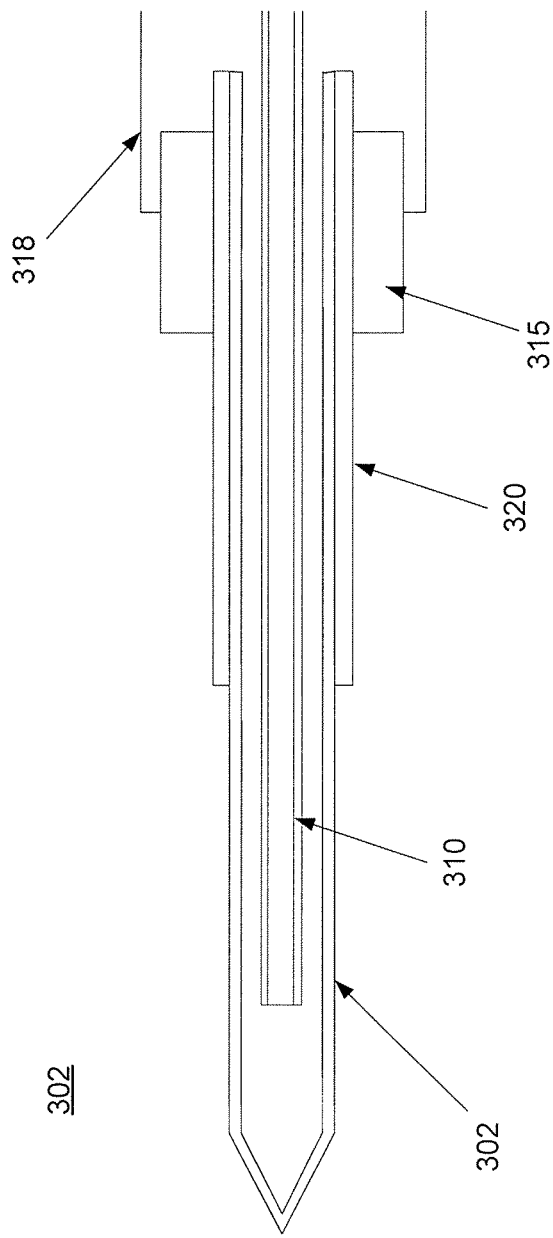

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 5 cm, preferably having a length from about 0.3 cm to about 0.6 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive heater block 315 with heat conductive epoxy allows temperature monitoring. Other temperature sensors may also be used, such as a thermocouple.

A cladding 320 of conductive material is directly conductively coupled to the proximal portion of the shaft of needle shaft 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2 mm. In some embodiments, the cladding 320 be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer (e.g., PTFE) or metal coating can cover the cladding to promote biocompatibility of an otherwise non-biocompatible but highly conductive cladding material and/or to promote lubricity of the needle probe. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

Figure 3C:
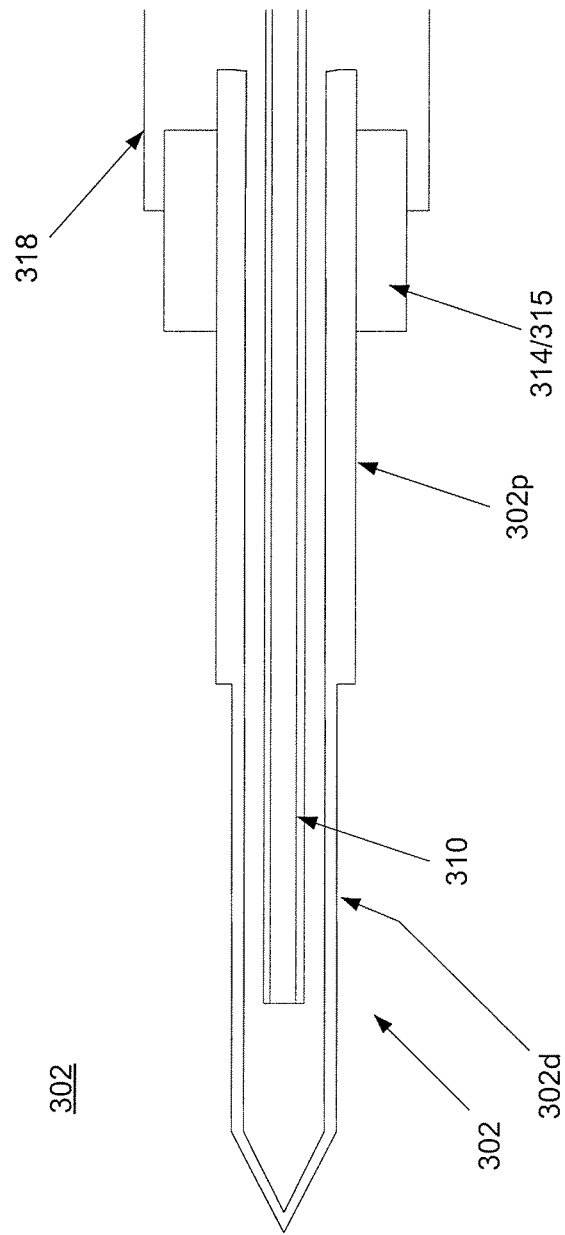

FIG. 3C illustrates a cross-section of the needle shaft 302 of needle probe 300, according to an alternative embodiment. The needle shaft 302 is substantially identical to what is depicted in FIG. 3B. However, instead of a cladding, the needle shaft 302 has a proximal shaft portion 302p that is a greater wall thickness than the distal portion 302d. As shown, the proximal portion 302p has a larger outer diameter than that of the distal portion 302d, while both share the same inner diameter. In some embodiments, the proximal portion 302p and distal portion 302d share the same outer diameter, with the proximal portion 302p having a smaller inner diameter than the distal portion 302d. In some embodiments, the outer diameter of the proximal portion 302p can gradually taper down to the outer diameter of the distal portion 302d in a continuous manner over a discrete or entire length of the needle shaft. In all of these embodiments, the proximal portion 302p has more mass than the distal portion 302d, and thus more conductive as compared to the distal portion 302d.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing latent heat to pressurized cryogenic cooling fluid passing within the proximal portion of the needle to affect complete vaporization of the fluid. Thus, the non-target tissue in contact with the proximal portion of the needle shaft 302 does not need to supply latent heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

Figure 3D:
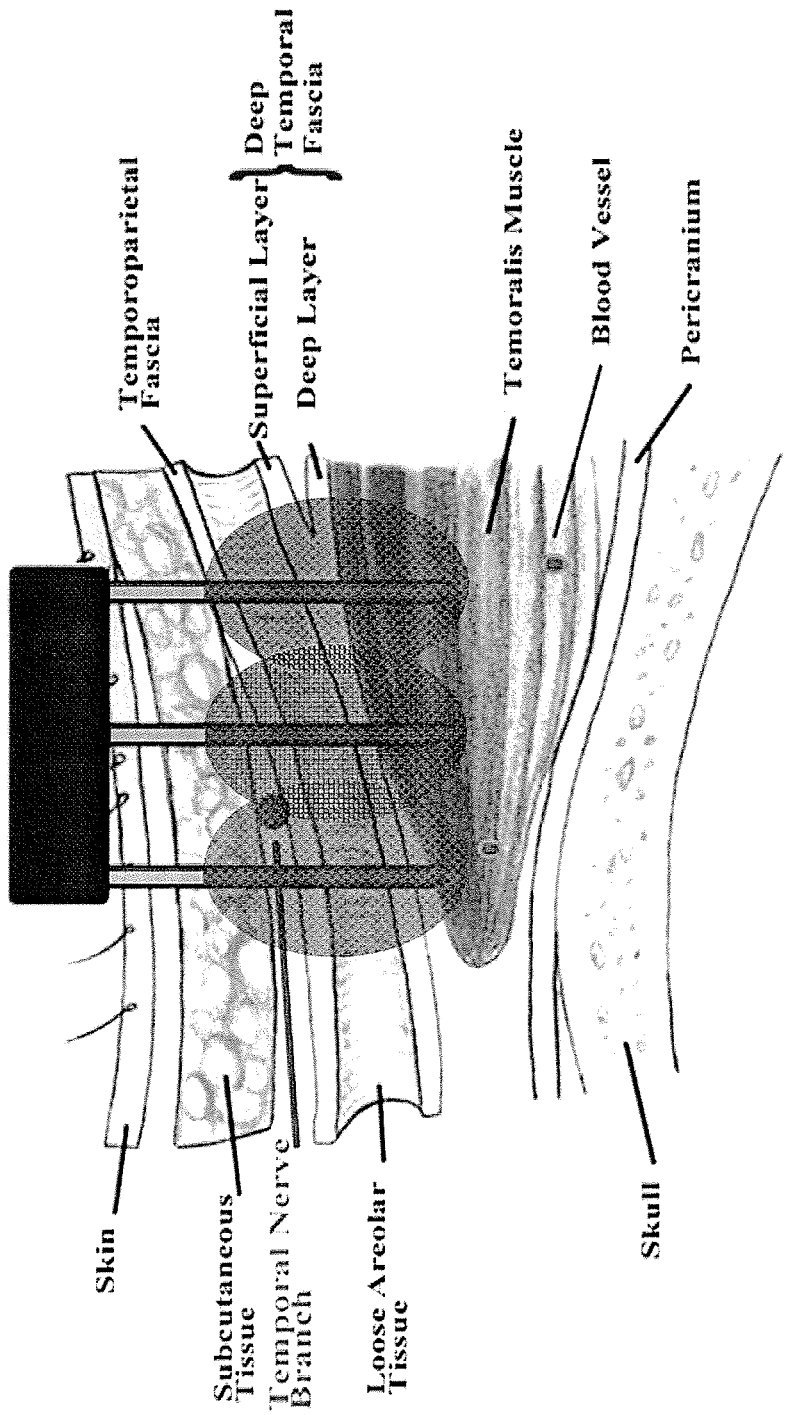
FIG. 3D illustrates a portion of a method for using the clad needle probe of FIGS. 3A-3C, according to an embodiment of the invention.

In use, it has been determined experimentally that the cladding 320 can help limit formation of an cooling zone to the distal portion of the needle shaft 302, which tends to demarcate at a distal end of the cladding 320. This effect is shown depicted in FIG. 3D where non-target tissue, directly above target tissue, including skin and at least a portion of subcutaneous tissue are not made part of the cooling zone. Rather, cooling zones are formed only about the distal portions of the needles—in this case to target a temporal nerve branch. Thus, while non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Standard stainless steel needles and gold clad steel needles were tested in porcine muscle and fat. Temperatures were recorded measured 2 mm from the proximal end of the needle shaft, about where the cladding distally terminates, and at the distal tip of the needles. As shown, temperatures for clad needles were dramatically warmer at the 2 mm point versus the unclad needles, and did not drop below 4° C. The 2 mm points of the standard needles however almost equalize in temperature with the distal tip.

Figure 4:
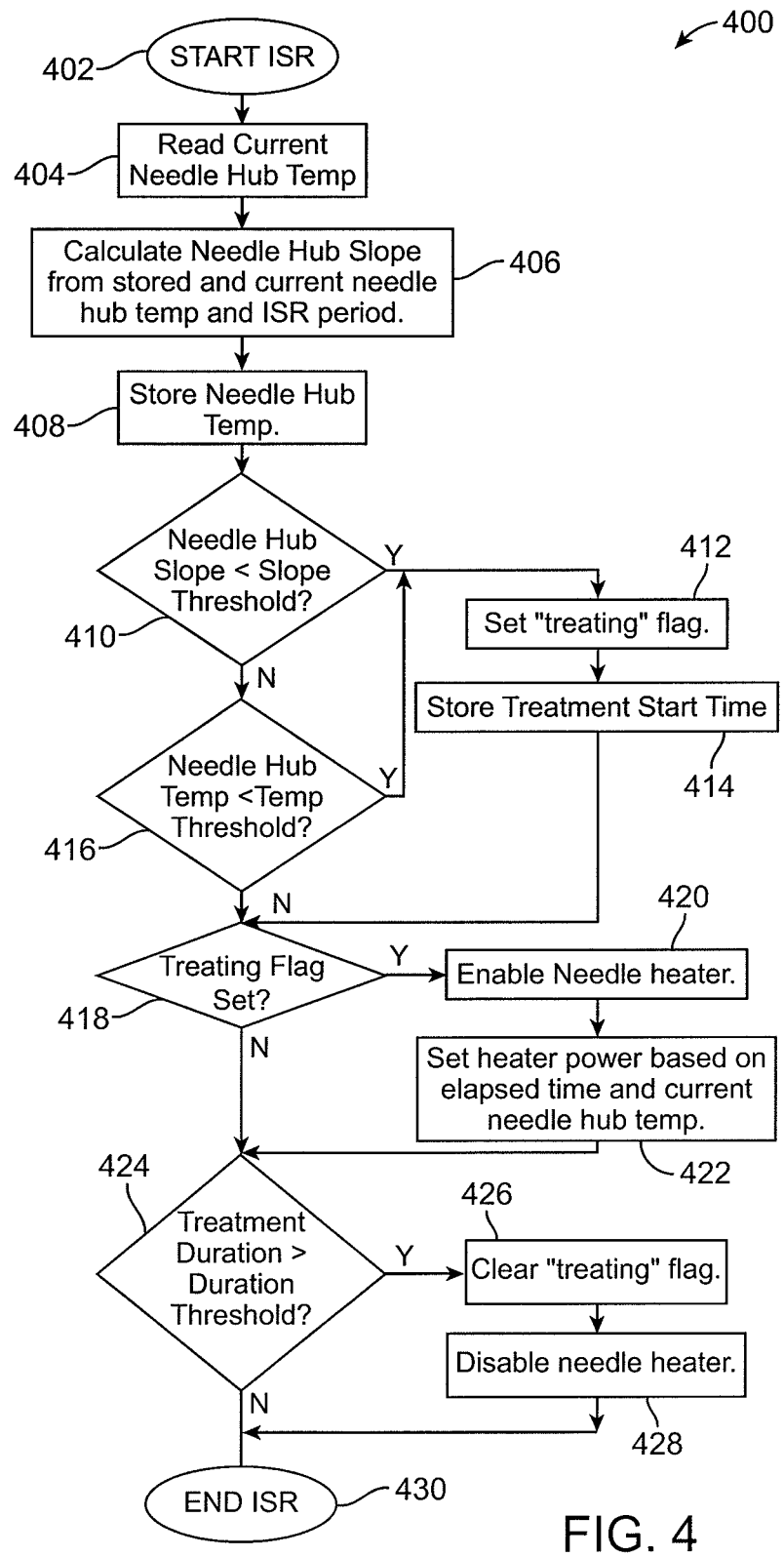
FIG. 4 is a flow chart illustrating an exemplary algorithm for heating the needle probe of FIG. 3A.

An exemplary algorithm 400 for controlling the heater element 314, and thus for transferring heat to the cladding 320, is illustrated in FIG. 4. In FIG. 4, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a noun, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment, may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds and more preferably may range from about 15 seconds to about 60 seconds.

It should be appreciated that the specific steps illustrated in FIG. 4 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
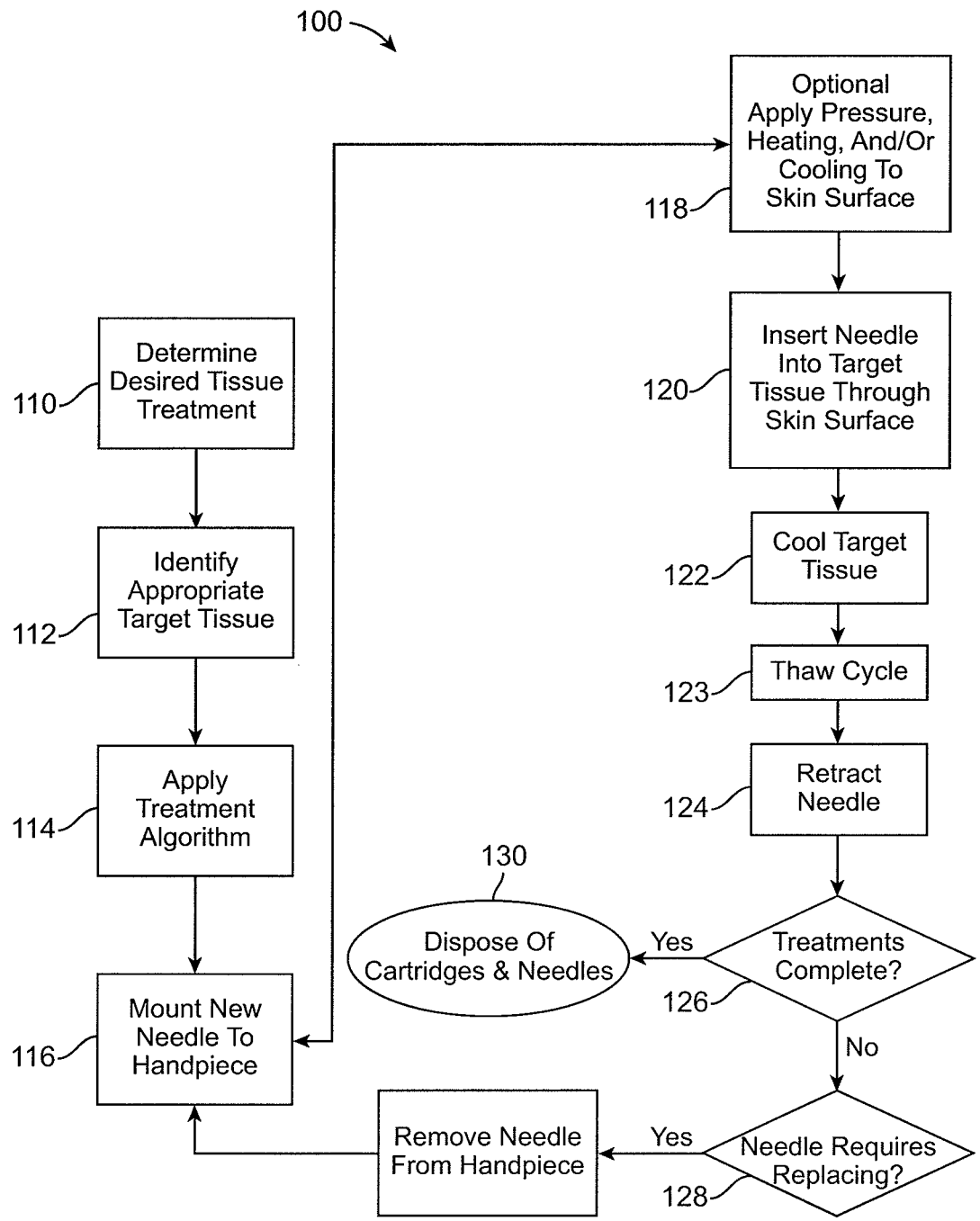
FIG. 5 is a flow chart schematically illustrating a method for treatment using the disposable cryogenic probe and system of FIG. 1B.

The heating algorithm may be combined with a method for treating a patient. Referring now to FIG. 5, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. The application of the treatment algorithm 114 may include the control of multiple parameters such as temperature, time, cycling, pulsing, and ramp rates for cooling or thawing of treatment areas. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include; but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

A variety of target treatment temperatures, times, and cycles may be applied to differing target tissues to as to achieve the desired remodeling. For example, (as more fully described in U.S. Patent Publication Nos. 2007/0129714 and 2008/0183164, both previously incorporated herein by reference.

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the claims as follows.

What is claimed is:

1. A method for cryogenically treating tissue, the method comprising:
   providing a needle probe shaft having a distal portion and a proximal portion, the needle probe shaft comprising a first conductivity at the distal portion and a second conductivity at the proximal portion, wherein the proximal portion extends axially along a longitudinal axis of the needle probe shaft, and wherein the second conductivity is greater than the first conductivity;
   advancing the needle probe shaft into non-target tissue layered above target tissue, such that the distal portion of the needle probe shaft is positioned within the target tissue and the proximal portion of the needle probe shaft is positioned within the non-target tissue
   cooling the target tissue via the distal portion of the needle probe shaft to affect remodeling of the target tissue; and
   directly conducting energy to the proximal portion of the needle probe shaft while cooling the target tissue, thereby limiting cooling of the non-target tissue.

2. The method of claim 1, wherein the non-target tissues includes skin.

3. The method of claim 2, wherein limiting cooling prevents discoloration of the skin.

4. The method of claim 2, wherein the non-target tissues includes at least a portion of subcutaneous tissue.

5. The method of claim 1, wherein cooling zones formed in the target tissue terminate proximally about a distal end of a second conductive material.

6. The method of claim 1, wherein remodeling the tissue causes nerve signal conduction disruption within the target tissue.

7. The method of claim 1, wherein the needle probe shaft comprises a first conductive material at the distal portion and a second conductive material at the proximal portion, wherein the second material is more conductive than the first material.

8. The method of claim 7, wherein the second conductive material is conductively coupled to a heat source.

9. The method of claim 8, wherein the heat source provides the second conductive material with 0.5-3 W during cooling.

10. The method of claim 7, wherein conducting energy provides energy to affect a phase change of a liquid coolant to a gas at the proximal portion.

11. The method of claim 7, wherein the first conductive material comprises stainless steel.

12. The method of claim 11, wherein the second conductive material comprises at least one layer of metal over the stainless steel.

13. The method of claim 12, wherein the at least one layer of metal comprises gold.

14. The method of claim 1, wherein the proximal portion of the needle probe shaft has greater mass than the distal portion of the needle probe shaft.

15. The method of claim 14, wherein the proximal portion of the needle probe shaft has a greater wall-thickness than the distal portion of the needle probe shaft.

16. A method for cryogenically treating tissue, the method comprising:
- providing a needle probe shaft having a distal portion and a proximal portion, the needle probe shaft comprising a first conductive material and a cladding layer extending axially along a longitudinal axis of the needle probe shaft and along an outer surface of the proximal portion of the needle probe shaft, wherein the cladding layer comprises a second conductive material conductively coupled to the first material at the proximal portion, wherein the second material is more conductive than the first material;
- advancing the needle probe shaft into non-target tissue layered above target tissue, such that the distal portion of the needle probe shaft is positioned within the target tissue and the cladding layer of the needle probe shaft is positioned within the non-target tissue
- cooling the target tissue via the distal portion of the needle probe shaft to affect remodeling of the target tissue; and
- directly conducting heat energy to the cladding layer of the needle probe shaft while cooling the target tissue, thereby limiting cooling of the non-target tissue.

\* \* \* \* \*